United States Patent [19]

Jones

[11] 4,128,597
[45] Dec. 5, 1978

[54] ALKYLATION PROCESS UTILIZING HYDROCARBON PHASE FOR COOLING AND COMPRESSED VAPOR FOR SUPPLYING HEAT TO DISTILLATION COLUMN

[75] Inventor: Richard H. Jones, South Euclid, Ohio

[73] Assignee: The Standard Oil Company, Cleveland, Ohio

[21] Appl. No.: 845,762

[22] Filed: Oct. 26, 1977

Related U.S. Application Data

[63] Continuation-in-part of Ser. No. 742,949, Nov. 18, 1976, which is a continuation-in-part of Ser. No. 650,341, Jan. 19, 1976, abandoned, and Ser. No. 650,342, Jan. 19, 1976.

[51] Int. Cl.² ............................................. C07C 3/54
[52] U.S. Cl. ............................................. 260/683.62
[58] Field of Search ................... 260/683.59, 683.62, 260/683.58, 683.48, 683.43, 683.4 F

[56] References Cited

U.S. PATENT DOCUMENTS

| Re. 26,060 | 7/1966 | Nathan | 260/683.62 |
| 2,345,742 | 4/1944 | Gardner | 260/683.43 |
| 3,215,752 | 11/1965 | Vermillion, Jr. | 260/683.62 |
| 3,925,501 | 12/1975 | Putney et al. | 260/683.48 |
| 3,970,720 | 7/1976 | West | 260/683.4 F |

Primary Examiner—George Crasanakis
Attorney, Agent, or Firm—David J. Untener; Herbert D. Knudsen; Larry W. Evans

[57] ABSTRACT

In the process for the catalytic alkylation of isobutane with an olefin to produce alkylate, the liquid reactor effluent stream comprising a hydrocarbon mixture of alkylate, isobutane and inert alkanes is partially vaporized by providing cooling to various condensers in the alkylation process. The vapors are then recovered, compressed and used to provide heat to various distillation columns found in the process.

20 Claims, 3 Drawing Figures

ALKYLATION PROCESS UTILIZING HYDROCARBON PHASE FOR COOLING AND COMPRESSED VAPOR FOR SUPPLYING HEAT TO DISTILLATION COLUMN

CROSS-REFERENCE TO RELATED APPLICATIONS

This is a continuation-in-part of Ser. No. 742,949 filed Nov. 18, 1976 which is a continuation-in-part of abandoned application Ser. No. 650,341, filed Jan. 19, 1976 and Ser. No. 650,342 filed Jan. 19, 1976, the disclosures of which are incorporated herein by reference.

BACKGROUND OF THE INVENTION

Catalytic alkylation of isobutane is well known in the art, being the union of an olefin with isobutane in the presence of an acid catalyst to produce high octane branched chain hydrocarbons (alkylate) for use in aviation gasoline and motor fuel. Specifically, the olefin is combined with isobutane in the presence of an acid catalyst in a reactor and undergoes an exothermic reaction. The acid is then separated from the reactor effluent. After acid separation, the reactor effluent proceeds to a series of distillation columns to separate the inert alkanes, the unreacted isobutane for recycle, and to recover the alkylate. Treating is also performed on some of the effluent to remove residual acid and undesired reaction products. A variation of this process has been to use the vaporization of a portion of the reactor effluent to cool the reactor, see *Hydrocarbon Processing*, September, 1974, page 206.

The vapors produced by cooling the reactor have been used to supply heat to a deisobutanizer distillation column. U.S. Pat. Nos. 3,162,694 and Re 26.060 disclose such a process. These processes however, suffer from several disadvantages.

First, the amount of vapors produced by cooling the reactor are normally not sufficient to supply the total heat necessary to the deisobutanizer. Secondly, the normally high operating pressures of the distillation columns makes it difficult to use these vapors as a source of heat.

The present invention solves the disadvantages of the existing art by using the reactor effluent to cool the overhead vapor streams of the distillation columns found in the process. This allows the distillation columns to operate at a much lower pressure. The increased vapors of the reactor effluent produced by cooling the distillation column overheads, along with the lower operating pressure of these columns, allows the total energy input to the process to be greatly reduced.

SUMMARY OF THE INVENTION

The invention is in a process for catalytic alkylation of isobutane with an olefin comprising:
(a) contacting said olefin with a molar excess of isobutane and inert alkanes in the presence of an acid catalyst in a reactor to form a reactor effluent containing alkylate, isobutane, acid catalyst and inert alkanes;
(b) separating said acid catalyst from said reactor effluent to form a hydrocarbon mixture;
(c) effecting a liquid vapor separation on a portion of said hydrocarbon mixture to obtain a liquid bottoms stream containing isobutane and alkylate and an overhead vapor stream containing isobutane and inert alkanes;
(d) heating in a distillation zone said liquid bottoms stream to form a liquid bottoms product containing alkylate and a vaporous distillation effluent containing isobutane separated from said alkylate;
(e) passing a portion of said hydrocarbon mixture as a cooling effluent in indirect heat exchange with said vaporous distillation effluent to condense isobutane and to vaporize at least a portion of said cooling effluent;
(f) admixing said cooling effluent with said portion of the hydrocarbon mixture in step (b) so that said cooling effluent is subjected to liquid vapor separation along with said portion of the hydrocarbon mixture in step (c);
(g) compressing the overhead vapor stream produced in step (c) in a compressor to obtain a compressed vapor stream; and
(h) passing at least a portion of said compressed vapor stream in indirect heat exchange relation with liquid in said distillation zone of (d) to condense at least a portion of the compressed vapor stream and thereby supply heat to said distillation zone.

A further embodiment of the invention is in a process for separating inert alkanes and isobutane from a gaseous alkylation reactor effluent containing alkylate, isobutane and inert alkanes comprising:
(a) effecting a liquid vapor seaparation on a portion of said reactor effluent to obtain a overhead vapor stream containing isobutane and inert alkanes and a liquid bottoms stream containing isobutane and alkylate;
(b) compressing said overhead vapor stream;
(c) passing at least a portion of said compressed overhead vapor stream through a heat exchanger thereby at least partially condensing said compressed overhead vapor stream forming an exchanger effluent stream;
(d) passing a first portion of the exchanger effluent stream to an alkane distillation zone;
(e) heating the liquid in said alkane distillation zone by passing it in indirect heat exchange with the heat exchanger of (c), thereby distilling and separating inert alkane as a vaporous fraction and isobutane as a liquid bottoms product;
(f) passing a portion of said reactor effluent of (a) as a cooling effluent in indirect heat exchange with said vaporous fraction of (e) to condense the inert alkane therein and to vaporize a portion of said reactor effluent; and
(g) admixing said cooling effluent with said portion of the reactor effluent in step (a) so that said cooling effluent is subjected to liquid vapor separation along with said portion of the reactor effluent in step (a).

Using the present invention, the amount of isobutane that must be treated and recovered in the distillation column is greatly reduced, cooling water is no longer necessary for the distillation column overhead condenser, the distillation columns may be operated at substantially lower pressures, and a much greater heat transfer rate may be acquired between the compressed vapor stream and the distillation columns. Further, the compressed vapor stream can now supply heat to columns other than the deisobutanizer.

The invention is best understood by reference to the drawings.

DESCRIPTION OF THE DRAWING

Referring to FIG. 1, olefin and isobutane feed, in liquid phase, are combined in line 101 and fed to reactor 103 where the reactants are mixed with acid catalyst and reacted to form alkylate. The product leaves the reactor through line 105 to the acid separator 107. Here the acid is separated from the hydrocarbon mixture and returned to the reactor through line 108. The hydrocarbon mixture containing alkylate, isobutane and inert alkanes leaves the acid separator through line 109.

Figure 1:
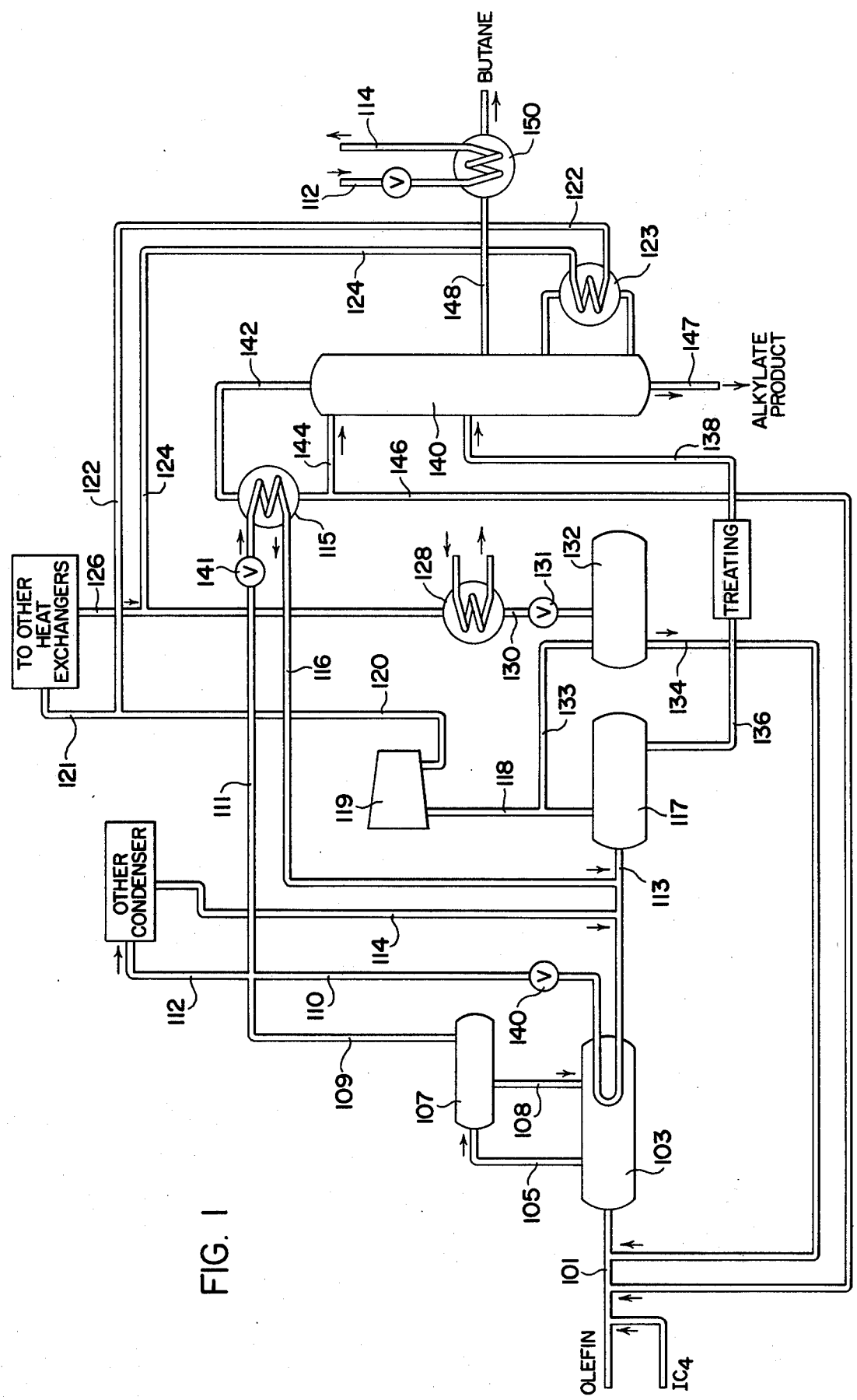
FIG. 1 shows the process as applied to a deisobutanizer distillation column.

The hydrocarbon mixture goes to provide cooling in the condensers through lines 111 and 112. Specifically referring to line 111, it is seen how the cooling function of the present invention is applied to the deisobutanizer column. Hydrocarbon mixture is transmitted through line 111 and reduced in pressure by valve 141. The mixture is then transmitted to condenser 115 where at least part of the hydrocarbon mixture is vaporized to provide cooling in the condenser. The hydrocarbon mixture after providing cooling is transmitted through line 116 to the vapor-liquid separator 117. Cooling may also be supplied to other condensers such as the depropanizer, shown in greater detail in FIG. 2, or the later described butane sidestream draw from the deisobutanizer column, by taking the hydrocarbon mixture through line 112, vaporizing at least part of the hydrocarbon mixture in the condenser, and transmitting the condensor effluent through line 114 to the vapor liquid separator 117. The hydrocarbon mixture can also be used to cool the reactor through line 110, being let down on pressure through valve 140. It is then transmitted through line 113 to the vapor liquid separator.

In the vapor liquid separator 117 a vapor liquid separation takes place. The vapor contains primarily isobutane and inert alkanes, and the liquid contains primarily isobutane and alkylates. However, some n-butane may be present in the liquid because of the boiling point of n-butane. The vapors are transmitted through line 118 to a vapor compressor 119. The compressed vapors leave the compressor through line 120. The compressed vapors then go to provide heating in exchangers through lines 121 and 122. Specifically referring to line 122, it is seen how the heating function of the present invention is applied to the deisobutanizer column. The compressed vapors are transmitted through line 122 to a heat exchanger 123 wherein at least part of the vapors are condensed to provide heat in the exchanger. The compressed vapors after providing heat, are transmitted through line 124 to a condenser 128. This condenser effects a condensation of the remaining vapors, and the condensed, compressed vapors are then transmitted through line 130 to a second vapor liquid separator 132. In the same manner, heat is supplied to the other exchangers, such as the depropanizer heat exchanger, by taking the compressed vapors through line 121, condensing at least part of the vapors in the exchanger and transmitting the exchanger effluent through line 126. This stream is then combined with line 124 prior to condenser 128.

The pressure in line 130 is maintained by valve 131. The condensed stream leaving condenser 128 through line 130 is reduced in pressure and thus partially vaporized by valve 131 prior to its entry in the second vapor liquid separator 132. Vapors are removed from the separator through line 133 and combined with line 118 back to the compressor. These vapors may be returned to the suction of the compressor, or some intermediate point within the compressor stages. The liquid from the second vapor liquid separator contains isobutane and some inert alkanes and is transmitted through line 134 back to the reactor to provide excess isobutane for the reaction.

The liquid from the first vapor liquid separator 117 containing isobutane and alkylate proceeds through line 136 to a treating section where residue acid and acidic compounds are removed. After treating, the liquid is transmitted through line 138 to the deisobutanizer column 140. Heat is applied to the column through heat exchanger 123 from the compressed vapors as described previously. Isobutane is distilled and exits the top of the column as a vapor in line 142. This vapor is condensed in the overhead condenser 115 and the condensed isobutane is then split for reflux to the column through line 144, and is recycled to the reactor through line 146. The alkylate product is recovered as a liquid bottoms stream from the column through line 147.

Also shown on the drawing is the optional use of recovering butane as a sidestream draw from the deisobutanizer column 140. Vapors are removed through line 148 and transmitted to condenser 150. The reactor effluent can be used as the cooling medium through line 112 and 114 to condense the butane. Butane is then recovered as a product from this condenser.

Figure 2:
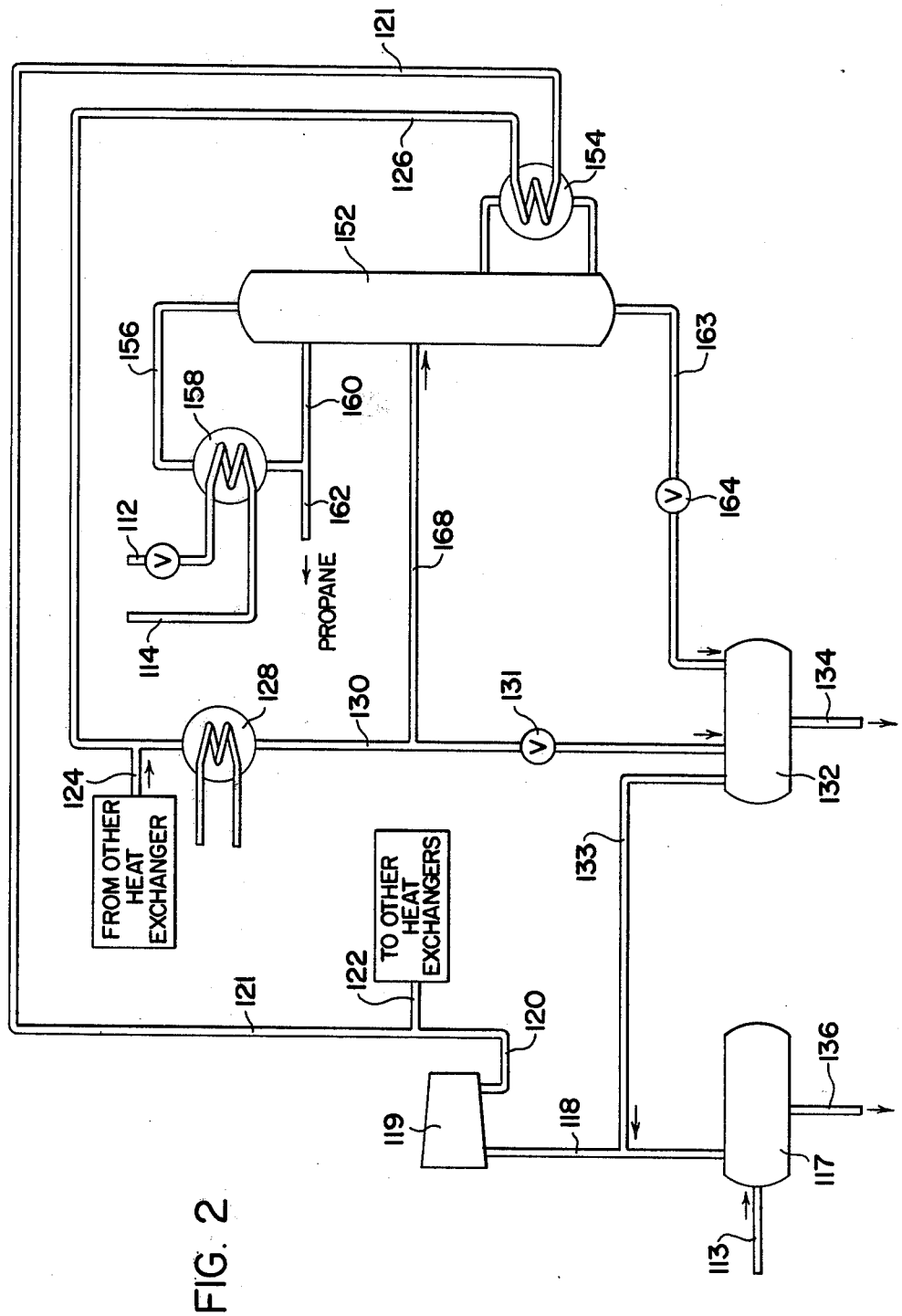
FIG. 2 shows the invention being applied to a depropanizer distillation column.

Referring to FIG. 2 it is seen how the cooling and heating functions of the present invention is applied to the processes that have depropanizer distillation columns. The numbers of similar lines and equipment that appear in FIG. 1 have been kept the same.

The reactor effluent, after being used as a coolant, enters the first vapor liquid separator 117 through line 113. A liquid bottoms stream containing isobutane and alkylate is removed through line 136 and sent to further processing as shown in FIG. 1. The vapors from the vapor liquid separator are transmitted through line 118 to compressor 119. The compressed vapors exit the compressor through line 120. The compressed vapors then go to provide heating in exchangers through lines 121 and 122. Specifically referring to line 121 it is seen how the present invention is applied to the depropanizer column. The compressed vapors are transmitted through line 121 to a heat exchanger 154 where at least part of the vapors are condensed to provide heat to the exchanger. The compressed vapors after providing heat are transmitted through line 126. This is combined with vapors that have exchanged heat in other exchangers returning in line 124, and transmitted to condenser 128. The condensed vapor stream leaves the condenser through line 130. A portion is taken through line 168 as feed to the depropanizer distillation column 152. Heat is applied to this column as described previously through heat exchanger 154. Propane is distilled and exits the top of the column as a vapor in line 156. This vapor is then condensed in condenser 158 by the use of the reactor effluent in lines 112 and 114. The condensed propane is then split into line 160 as reflux to the column, and line 162 as propane product. The isobutane-rich bottoms leaves the depropanizer column through line 163, is let down in pressure through valve 164 and then transmitted to the second vapor liquid separator 132. The condensed vapors from condenser 128 that is not sent to the depropanizer column is also let down in pressure through valve 131 and transmitted to the second vapor liquid separator 132. The vapors are removed from this separator through line 133 and recycled back to the compressor as disclosed in FIG. 1. The liquid bottoms stream 134, containing mostly isobutane, can be recycled back to the reactor as also shown in FIG. 1.

Figure 3:
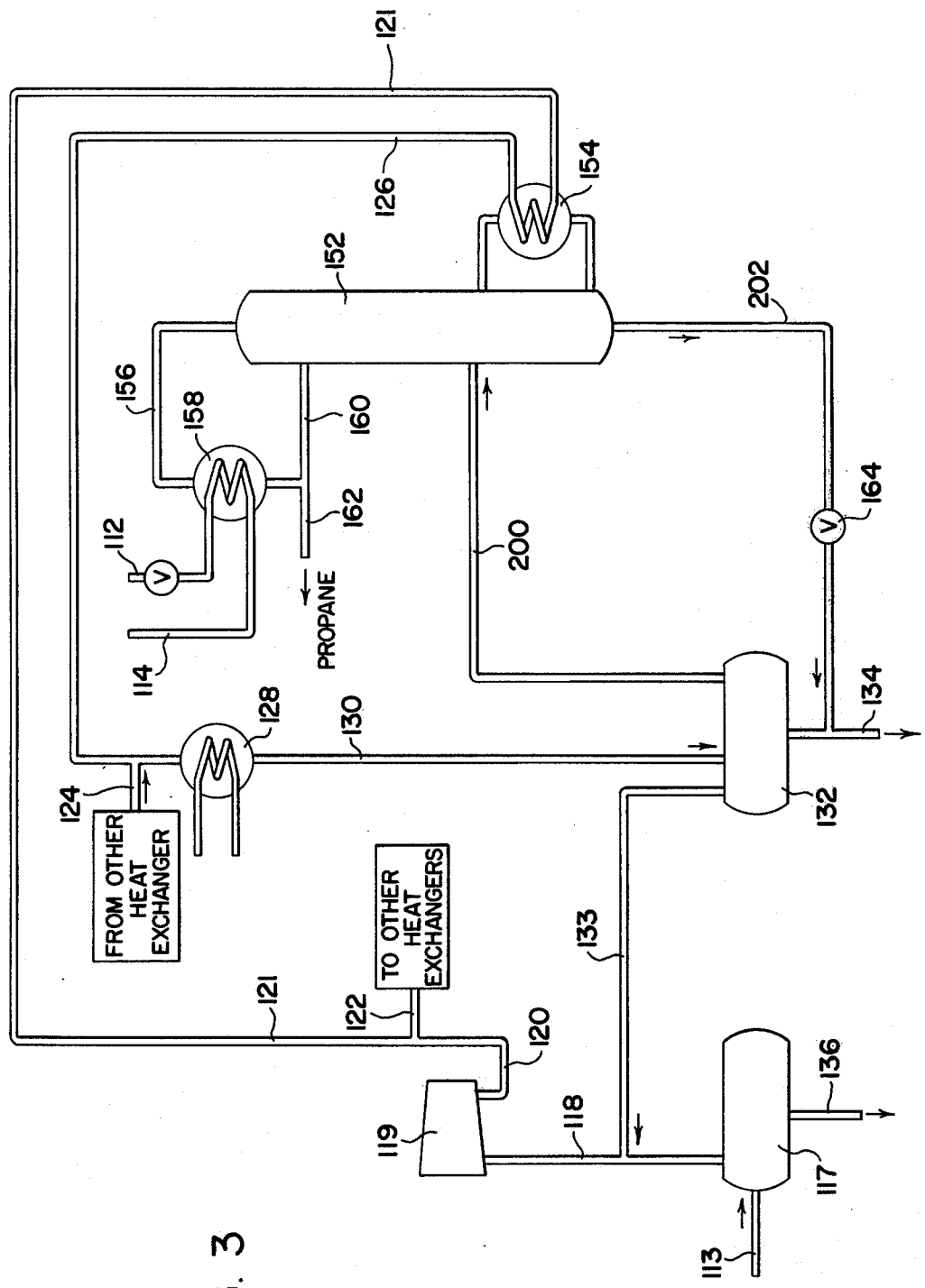
FIG. 3 discloses an alternate embodiment of FIG. 2.

FIG. 3 represents an alternate and preferred method of the system shown in FIG. 2.

The primary difference between FIGS. 2 and 3 is that the compressed vapors, after supplying heat to the depropanizer, are not totally condensed in condenser 128.

The partially condensed vapor stream leaves the condenser 128 through line 130 and is sent to the vapor-liquid separator 132. The uncondensed vapors are then transmitted through line 200 as feed to the depropanizer. Thus the feed to the depropanizer, being a liquid stream in FIG. 2 is now a vapor stream.

The isobutane-rich bottom stream leaves the depropanizer column through line 202 and is recycled back to the reactor. This stream can be combined with the isobutane in line 134 from the vapor-liquid separator.

The present invention has many advantages over the art. By combining the heating and cooling functions large energy savings may be required.

Cooling the overhead of the distillation columns by using the reactor effluent increases the amount of isobutane that is vaporized in the reactor effluent and need not be distilled. This reduces the size of the distillation columns and the amount of heat necessary to perform distillation. It also allows the distillation columns to be operated at a much lower pressure than presently exists in the art. By increasing the vapor flow and reducing the pressure in the distillation columns the compressed vapors can be used to supply the heat necessary for the distillation columns. Thus a unique savings is made in utilities because the water used to condense the overhead distillation column is no longer necessary, and the external heat supplied to the columns is greatly reduced or eliminated.

DESCRIPTION OF PREFERRED EMBODIMENT

In the preferred concept of this invention, the reactor effluent, after acid separation, is sent to the overhead condensers on the distillation columns of the process to provide cooling. The compressed vapors from the first vapor liquid separator is sent to the bottom heat exchangers to the distillation columns to provide heat. This concept is preferred because lower temperatures can be achieved in the columns using the reactor effluent then by using cooling water. With lower temperatures and pressures in the columns the separation process is greatly enhanced and the amount of heat input to achieve this separation is reduced.

Typically, at least two distillation columns are present, a deisobutanizer for separating isobutane from the alkylate product, and a depropanizer to recover the lighter propane from the deisobutane. In some cases a third column for separating butane from alkylate is present. The use of the present invention on this tower is also contemplated. However, butane may also be removed as a sidestream draw from the deisobutanizer column as shown in the drawings.

After exchanging heat, the compressed vapor stream can be further condensed by a small cooler to remove the heat that cannot be economically recovered through heat exchange. After the stream is condensed, it can then be let down in pressure and sent to a vapor liquid separator. This separator removes as a vapor any uncondensed and lighter boiling components and recycles them back to the vapor compressor. The isobutane-rich liquid remaining in the separator can then be recycled back to the reactor.

The discharge pressure of the vapor compressor may be that presently used in the art. However, the invention contemplates a compressed vapor stream pressure of between 50-200 psig, preferred pressure being about 150 psig. This pressure will vary according to the amount of heat transfer desired at a given distillation column. The higher the pressure of the distillation column the higher the discharge pressure of the vapor compressor. Thus it is advantageous to run the distillate columns at lower pressures that can now be achieved in the prior art.

The reactor illustrated in the figures is a conventional liquid phase alkylation reactor. The reactor may however, also be a two phase cascade reactor wherein the reaction zone is directly refrigerated by evaporation of low boiling hydrocarbons. In this type of reactor, the acid separation and vapor-liquid separation take place within the reactor itself. The vapors are removed from the reactor, compressed and then used to supply heat to the distillation columns. The liquid from the reactor, removed as a separate stream, can be used to condense the overhead of the distillation columns.

The deisobutanizer column may be operated at pressures between 1 and 150 psig but it is preferred to operate at a pressure between 30-50 psig. The depropanizer distillation column may be operated at a pressure between 50 and 150 psig with a preferred pressure between 75-125 psig.

It is anticipated this invention may be used in any catalytic alkylation process involving an acid catalyst. The acid catalyst that may be used are known in the art, including but not limited to sulfuric and hydrofluoric acid. Preferred in the present invention is the use of sulfuric acid catalyst.

The reaction conditions and parameters are not significantly changed by this invention. Normally the reactor is operated between 1-200 psig, and a temperature between −10° to 50° C.

The olefin feed to the alkylation process is also known in the art and is not affected by the present invention. Normally the composition of the olefin feed depends on the specific application, but may comprise propylene, butylenes or amylenes. The olefin feed may also contain various inert alkanes, such as propane and butane. The olefin is mixed with isobutane either before going to the reactor or in the reactor. Normally the higher the ratio of isobutane to olefin in the feed stock the greater the yield of alkylate. This external ratio is usually about 5:1 but can be 15:1 or higher. The present invention takes advantage of this ratio by recovering isobutane for recycle in a more efficient and less costly manner than the present art. By using this invention in existing units this ratio can be increased, thereby improving the octane of the product without being limited by the size of the deisobutanizer. Further, the use of a higher ratio also reduces acid consumption during the reaction.

As shown in the drawings, the reactor effluent used to provide cooling may be passed through a pressure-reducing valve prior to its entry into the various condensers. The pressure is reduced sufficiently to permit vaporization and effect greater cooling in the condenser. The pressure may be reduced to a pressure of 1 psia to about 50 psia. It is preferred to reduce this pressure of 3 psig to about 5 psig.

SPECIFIC EMBODIMENT

Example 1 and Comparative Example A

A computer simulation was made of an alkylation process as depicted in the *Hydrocarbon Processing* reference of September, 1974, page 206. Sulfuric acid was used as the acid catalyst. The reactant feed to both examples was 1955 barrels per stream day (BPSD), being a combination of isobutane, butylene and inert alkanes.

For comparison, the amount of product and its octane number were held constant for both examples. Due to the larger amounts of inert alkanes that are recycled in the effluent refrigeration stream of the present invention, the isobutane/olefin ratio in the reactor increased when compared to the art. The other operating conditions of the reactor were the same for both examples.

Comparative Example A shows the present art. The reactor effluent after acid separation was used to cool the reactor. After cooling, the effluent stream was sent to the first vapor-liquid separator. The liquid from this separator constituted the stream that was treated and sent as feed to the deisobutanizer column. Cooling water was used as the cooling medium in the overhead condenser of this column. The vapors from the vapor liquid separator were compressed and condensed and used as feed to the depropanizer. Cooling water was used as the cooling medium in the overhead condenser of the depropanizer. Steam was used as an external heating source to both columns.

In Example 1, showing the present invention, the reactor effluent was sent in a parallel manner to the overhead condensers of the deisobutanizer and depropanizer columns. After cooling, the reactor effluent was collected in the first vapor liquid separator. The compressed vapors from the vapor liquid separator were used to supply the total heat to the depropanizer column. The vapors also supplied partial heat to the deisobutanizer column by using a side reboiler. The compressor discharge pressure using the present invention was 145 psia. The reboiler temperatures for the depropanizer and the deisobutanizer columns were 127° F. and 195° F. respectively.

The results of these two experiments are shown in the following table.

TABLE I

Comparison of Art Alkylation with Invention

|  | Art | Invention |
|---|---|---|
| Feed BPSD | 1955 | 1955 |
| IC$_4$/olefin ratio | 13.9 | 16.7 |
| Deisobutanizer |  |  |
| Feed BPSD | 10,199 | 6,266 |
| Column Diam. ft. | 7.5 | 4.5 |
| Top pressure psia | 140 | 35 |
| External heat* | 32.3 | 2.5 |
| Heat from vapors* | — | 6.5 |
| Total heat* | 32.5 | 9.0 |
| Depropanizer |  |  |
| Feed BPSD | 3,026 | 4,513 |
| Top pressure psia | 250 | 100 |
| External Heat | 4.5 | 0 |
| Heat from vapors | 0 | 4.6 |
| Total External Heat* | 37.5 | 13.6 |

*MM Btu/hr.

As shown in the table, far more of the isobutane contained in the reactor effluent is vaporized than is found in the prior art, allowing for a more efficient recovery.

The feed to the deisobutanizer column decreased from 10,199 to 6,266 barrels per stream day. This reduction in feed allowed for a much smaller column. The cooling function of the invention allowed the tower to be operated at a much lower pressure (35 psia) and resulted in a 66% reduction in the total heat necessary to this column. The Table also shows that the heat from the compressed vapors can now supply a large amount of the heat necessary to reboil this column.

Although the feed to the depropanizer increased due to the increased amount of vapors produced, use of the cooling function of the invention allowed the tower pressure to be reduced from 250 to 100 psia. This substantial reduction in pressure allowed the use of the compressed vapors to supply heat to this column. As the Table shows, all of the heat required by the depropanizer column can be supplied from the compressed vapors.

Of primary importance is the fact that the total heat to the process from an external source was reduced by 66%.

I claim:

1. A process for catalytic alkylation of isobutane with an olefin comprising the steps of:

(a) contacting said olefin with a molar excess of isobutane and inert alkanes in the presence of an acid catalyst in a reactor to form a reactor effluent containing alkylate, isobutane, acid catalyst and inert alkanes;

(b) separating said acid catalyst from said reactor effluent to form a hydrocarbon mixture;

(c) effecting a liquid vapor separation on a portion of said hydrocarbon mixture to obtain a liquid bottoms stream containing isobutane and alkylate and an overhead vapor stream containing isobutane and inert alkanes;

(d) heating in a distillation zone said liquid bottoms stream to separate a liquid bottoms product containing alkylate and a vaporous distillation effluent containing isobutane;

(e) passing a portion of said hydrocarbon mixture from step (b) as a cooling effluent in indirect heat exchange with said vaporous distillation effluent in an overhead condenser for said distillation zone to condense isobutane in said vaporous distillation effluent and to vaporize at least a portion of said cooling effluent;

(f) admixing said cooling effluent from step (e) with said portion of the hydrocarbon mixture of step (c) so that said cooling effluent is subjected to liquid-vapor separation along with said portion of the hydrocarbon mixture in step (c);

(g) compressing the overhead vapor stream produced in step (c) in a compressor to obtain a compressed vapor stream; and (h) passing at least a portion of said compressed vapor stream in indirect heat exchange relation with a liquid separated from said distillation zone of (d) to condense at least a portion of the compressed vapor stream and to supply heat to said distillation zone.

2. The process of claim 1 wherein a portion of said cooling effluent is additionally vaporized by reducing the pressure of said cooling effluent prior to the indirect heat exchange of step (e).

3. The process of claim 1 including the step of removing residual acid and impurities from said liquid bottoms stream of (d) prior to distilling said stream.

4. The process of claim 1 wherein a portion of said condensed compressed vapor stream of (h) is recycled to said reactor.

5. The process of claim 1 including the step of distilling in an alkane distillation zone a portion of said compressed vapor stream of (h) to remove inert alkanes therefrom as a vaporous alkane fraction and condensing the vaporous alkane fraction from said alkane distillation by passing said vaporous alkane fraction in indirect heat exchange with at least a portion of said cooling effluent.

6. The process of claim 5 wherein said inert alkane is propane.

7. The process of claim 1 wherein said liquid bottoms stream of (d) additionally contains normal butane and the distillation of said liquid bottoms stream includes the removal of normal butane as a vaporous sidestream and condensing said vaporous sidestream by passing it in indirect heat exchange with a second portion of said cooling effluent of (e).

8. The process of claim 5 including the step of passing at least a portion of said compressed vapor stream of (g) in indirect heat exchange with a liquid stream from the alkane distillation zone to condense at least a portion of the compressed vapor stream, thereby supplying heat to said alkane distillation zone.

9. The process of claim 1 wherein the compressed vapor stream of (h), after supplying heat to said distillation zone, is further condensed by cooling.

10. The process of claim 9 wherein the condensed compressed vapor stream is sent to a second vapor liquid separator wherein a vapor stream is removed overhead and recycled to the compressor of (g) and at least part of a liquid stream removed from the second vapor liquid separator is sent to the reactor of (a) as recycled isobutane.

11. The process of claim 1 wherein the compressed vapor stream of (g) is at a pressure of about 50–200 psig.

12. A process for separating inert alkanes and isobutane from a gaseous alkylation reactor effluent containing alkylate, isobutane and inert alkanes comprising:
 (a) effecting a liquid vapor separation on a portion of said reactor effluent to obtain an overhead vapor stream containing isobutane and inert alkanes and a liquid bottoms stream containing isobutane and alkylate;
 (b) compressing said overhead vapor stream;
 (c) passing at least a portion of said compressed overhead vapor stream through a heat exchanger thereby at least partially condensing said compressed overhead vapor stream forming an exchanger effluent stream;
 (d) passing a first portion of the exchanger effluent stream to an alkane distillation zone;
 (e) heating the liquid in said alkane distillation zone by passing it in indirect heat exchange with the heat exchanger of (c), thereby distilling and separating inert alkane as a vaporous fraction and isobutane as a liquid bottoms product;
 (f) passing a portion of said reactor effluent of (a) as a cooling effluent in indirect heat exchange with said vaporous fraction of (e) in an overhead condenser for said distillation zone to condense the inert alkane therein and to vaporize a portion of said reactor effluent; and
 (g) admixing said cooling effluent from step (f) with said portion of the reactor effluent in step (a) so that said cooling effluent is subjected to liquid vapor separation along with said portion of the reactor effluent in step (a).

13. The process of claim 12 wherein the exchanger effluent stream of (c) is passed in indirect heat exchange in a condenser to totally condense said exchanger effluent stream prior to passing a portion of said effluent stream to the alkane distillation zone.

14. The process of claim 12 wherein a portion of said cooling effluent of (f) is partially vaporized by reducing the pressure of said cooling effluent prior to the indirect heat exchange.

15. The process of claim 12 wherein the liquid bottoms product of (e) containing isobutane, and a second portion of the exchanger effluent stream of (c) containing isobutane and inert alkanes, is reduced in pressure and passed to a second vapor liquid separator, thereby forming a second overhead vapor stream containing isobutane and inert alkanes and a second liquid bottoms stream containing isobutane.

16. The process of claim 12 wherein the inert alkane is propane.

17. The process of claim 1 wherein the olefin is propylene.

18. The process of claim 1 wherein the olefin is selected from the group consisting of butylene or amylenes.

19. The process of claim 1 wherein the acid catalyst is a sulfuric acid.

20. The process of claim 12 wherein the portion of the exchanger effluent stream of (d) sent to said alkane distillation zone is a vapor.

* * * * *